United States Patent [19]

Shanbrom

[11] 4,412,985
[45] Nov. 1, 1983

[54] DEPYROGENATION PROCESS

[76] Inventor: Edward Shanbrom, 2252 Liane La., Santa Ana, Calif. 92705

[21] Appl. No.: 336,916

[22] Filed: Jan. 4, 1982

Related U.S. Application Data

[63] Continuation-in-part of Ser. No. 194,263, Oct. 6, 1980, Pat. No. 4,315,919.

[51] Int. Cl.$^3$ .......................... A61K 31/74; A61L 2/16
[52] U.S. Cl. ........................................ 424/78; 210/636;
422/28; 424/79; 424/85; 424/88; 424/89;
424/177; 424/180; 424/181; 424/183; 424/341;
424/343; 424/361; 424/366
[58] Field of Search ........................ 422/28; 210/636;
424/14, 78, 79, 85, 88, 89, 177, 180, 181, 183,
343, 361, 366, 341

[56] References Cited

U.S. PATENT DOCUMENTS 4,020,183  4/1977  Asculai ................................ 424/341
4,113,712  9/1978  Funakoshi ........................... 260/112
4,118,479  10/1978  Prince et al. ........................ 424/89
4,158,054  6/1979  Furminger et al. .................. 424/89

OTHER PUBLICATIONS

Sweadner et al., Appl. & Environ. Microbiol., vol. 34, No. 4 (1977) pp. 382-386.
Sweadner—Chem. Abst. vol. 87 (1977) p. 206,453e.
Skelly et al., Nature, vol. 290, 51-54, Mar. 5, 1981.

Primary Examiner—Sam Rosen
Attorney, Agent, or Firm—Eric P. Schellin

[57] ABSTRACT

Products and materials used in the biomedical field are depyrogenated by prolonged contact with a solution or suspension of about 0.1% to about 10% by weight of a nonionic amphiphile selected from the group consisting of substances having the general formula $RC_6H_4(OC_2H_4)_nOH$ wherein R is octyl or nonyl and n is at least 3, followed by liquid phase separation of said amphiphile from the resulting depyrogenated product or material.

9 Claims, No Drawings

DEPYROGENATION PROCESS

RELATED APPLICATION

This is a continuation-in-part of copending application Ser. No. 194,263, filed Oct. 6, 1980, now U.S. Pat. No. 4,315,919.

BACKGROUND OF THE INVENTION

This invention relates to a method of depyrogenating products and materials used in the biomedical field.

In the preparation of certain products and materials used in the biomedical field, the problem of contamination with pyrogens (endotoxins) is ever present.

Pyrogens are lipopolysaccharides (LPS) derived from the outer cell wall of gram-negative bacteria. They are toxic materials which are known as "endotoxins" to distinguish them from toxic substances synthesized and excreted by the intact bacterium. Pyrogens have numerous biologic activities which include the production of fever, activating of clotting mechanisms and induction of shock. Consequently, it is essential that pyrogenic substances be removed or inactivated and the causative bacteria be rendered innocuous by sterilization or other such treatment of the final biomedical product or material.

Prior methods for inactivation of pyrogens comprise extensive and rigorous treatment with heat, acid or alkali, filtration of insoluble pyrogens or removal by adsorption with gels, ion-exchange resins and various other such adsorbent materials. Most of these methods are burdensome, time-consuming and costly.

Further background information on the properties and effects of pyrogens can be had by reference to a paper by Elizabeth Work, entitled "Production, Chemistry and Properties of Bacterial Pyrogens and Endotoxins" in "Pyrogens and Fever", Ciba Foundation Symposium, 1971, pp. 23–47, edited by Wolstenholme and Birch, published by Churchill Livingstone; and a paper by D. C. Morrison and R. J. Ulevitch, entitled "The Effects of Bacterial Endotoxins on Host Mediation Systems" in *Amer. J. Pathol.* 93(2), 527–601 (1978).

Recently, in said copending application, Ser. No. 194,263, the present inventor disclosed a method of depyrogenating proteinaceous biological and pharmaceutical products. The method comprises treating said products by prolonged contact with a solution or suspension of a non-denaturing amphiphile, precipitating the proteinaceous product with a protein precipitant, and then separating from the precipitate the supernatant which contains the amphiphile and the dissociated or disaggregated endotoxin. Certain products and materials used in the biomedical field due to their non-proteinaceous nature or to their physical structure do not lend themselves well to precipitation with protein precipitants. That is, they are essentially non-precipitable by such methods or are preferably separated by means other than precipitation. In such cases, it is preferred to separate and remove the amphiphile and the dissociated or disaggregated endotoxin from the biomedical product or material by the improved methodology disclosed and claimed herein.

DESCRIPTION OF THE INVENTION

In accordance with the present invention, products and materials used in the biomedical field are depyrogenated by prolonged contact with a solution or suspension of from about 0.1% to about 10% by weight of a nonionic amphiphile selected from the group consisting of substances having the general formula $RC_6H_4(OC_2H_4)_nOH$, wherein R is octyl or nonyl and n is at least three, followed by liquid phase separation of said amphiphile from the resulting depyrogenated product or material.

As used herein, the term "amphiphile" is meant to define a substance containing both hydrophilic water-soluble and hydrophobic water-insoluble groups.

A preferred amphiphile of the foregoing general formula is octyl phenoxy polyethoxy ethanol. Nonionic substances of the latter type are available commercially from Rohm & Haas Co. under the trademark "Triton X", e.g., Triton X-100, Triton X-165, Triton X-205, Triton X-305 and Triton X-405. Another such nonionic substance is nonyl phenoxy polyethoxy ethanol which is available commercially under the trademark "Triton N-100."

Treatment of the biomedical product or material with the amphiphile can be carried out at any stage in the production sequence. Preferably, the depyrogenation treatment is carried out following the last step at which contamination with pyrogens is likely to occur. In those instances where pyrogen contamination occurs at a production stage following a previous depyrogenation, it may be necessary to subject the product or material to a further depyrogenation treatment in accordance with the methodology of this invention.

The period of time during which the biomedical product or material is contacted with the amphiphile should be sufficient to cause dissociation, disaggregation or inactivation of the endotoxin. Generally, a period of from about 30 minutes to about four hours at a temperature of from about 4° C. to about 37° C. is adequate to provide the desired dissociation, disaggregation or inactivation. However, longer periods of time are not harmful in most cases.

Testing for the presence of pyrogens to ensure adequate depyrogenation can be carried out by the standard qualitative fever response test in rabbits for pyrogens or by Limulus lysate amebocyte assay procedures for pyrogens (LAL tests). The latter tests are based on gelling of the lysate of the amebocytes of the horsehoe crab (*Limulus polyphemus*) by a pyrogenic preparation. See, e.g., U.S. Pat. Nos. 4,038,029; 4,096,091; 4,221,865–866 for typical examples of LAL tests.

The contact of the biomedical product or material with the amphiphile can be carried out by washing the product or material with a solution or suspension of the amphiphile, or by immersing or soaking the product or material in such solution or suspension, or by admixing with such solution or suspension.

The present invention is applicable to any non-proteinaceous or non-precipitable product or material in the biomedical field which because of its intended use in humans or use in the treatment of other products and materials intended to be used in humans or administered to humans for biomedical or therapeutic purposes should be free of pyrogens or otherwise sterile.

Examples of biomedical products and materials which can be depyrogenated in accordance with the present invention are:

Parenteral products such as non-proteinaceous, aqueous intravenous solutions such as, e.g., dextran, dextrose and mannitol;

Biomedical implants such as, e.g., heart valves, pumps and plastic or biological tubing;

Microfiltration and ultrafiltration equipment and materials which may be used for filtering biological and pharmaceutical products;

Chromatography and electrophoresis equipment and materials which may be used for the separation of biological and pharmaceutical products;

Filtration, gel-filtration and ion-exchange materials, including beads, fibers and membranes such as cotton, cellulose, nylon, dextran, agarose, Sephadex ® (crosslinked dextran), DEAE-Sephadex, DEAE-cellulose, Dowex ® and Amberlite ® ion-exchange resins (divinylbenzene cross-linked polystyrene), BioGel ® P (polyacrylamide gel) and other such materials used in the separation, purification and recovery pf antibiotics, vitamins, amino acids, peptides, proteins and the like substances;

Non-proteinaceous biological and pharmaceutical products which are heat and pH sensitive or otherwise can not be adequately depyrogenated by heat or pH adjustment such as antibiotics and heparin.

In accordance with another aspect of the invention, the depyrogenation and separation process can be applied to proteinaceous materials which do not lend themselves well to precipitation with protein precipitants or which preferably are separated from the amphiphile by means other than precipitation. Examples of such materials are nylon, nylon fibers and casein plastic materials. Other examples are low molecular weight peptides and proteins such as, e.g., interferon, protamine sulfate and the like substances.

The liquid phase separation of the amphiphile from the depyrogenated biomedical product or material can be carried out by various means such as, e.g., solvent washing or solvent phase extraction with a substance that is a solvent for the amphiphile but a nonsolvent for the biomedical product or material. Examples of suitable solvents are methanol, ethanol, isopropanol, butanol, chloroform, methylene chloride, toluene, xylene and other such organic solvents.

In some cases, chromatographic column separation techniques can be employed in which the depyrogenated product is adsorbed on an ion-exchange resin while the amphiphile passes through the column. The adsorbed product, e.g., protein, can then be eluted from the column by suitable elution techniques such as adjustment of pH and ionic concentration to release the adsorbed product.

Another suitable means for the liquid phase separation of the amphiphile from the depyrogenated product or material is by ultrafiltration. Ultrafiltration techniques are based on the ability of pressure-driven filtration membranes to separate multicomponent solutes, or solutes from solvents, according to molecular size, shape, and chemical bonding. Substances below a preselected molecular size are driven through the membrane by hydraulic pressure while larger molecules are held back. Such membranes can be tailored to provide greater than 90% retention of a particular molecular-weight solute (the retentate) while permitting complete passage of solutes (the permeate) whose molecular weights are only one half of that of the retained species. Suitable examples of such membranes are the Loeb type anisotropic cellulose acetate membranes as described, e.g., in U.S. Pat. Nos. 3,133,132 and 3,133,137. An example of a suitable ultrafiltration system for use in this invention is the Millipore Pellicon ® Cassette System available from Millipore Corporation.

The amphiphile also can be removed from the depyrogenated product or material by diafiltration or simple dialysis. In the case of compressible materials, e.g., cotton and wool fibers and fabrics, the depyrogenated product after removal from the treatment solution can be squeezed to wring out substantially all the remaining liquid phase.

In some cases, the amphiphile also can be removed after the depyrogenation processing by heating to its cloud point and then removing the resulting precipitate by phase separation.

The following examples will further illustrate the invention although it should be understood that the invention is not limited to these specific examples.

EXAMPLE 1

Depyrogenation of albumin solution followed by ultrafiltration

An aqueous solution of 4.5% human serum albumin (450 ml) was spiked with about 100 ng/ml (tested out to be 98 ng/ml) of endotoxin from E. coli. Triton X-100 was then added to a conentration of 2% and the mixture was incubated at room temperature (about 22°–25° C.). After 2 hours and then 4 hours of incubation, the endotoxin level was reduced to, respectively, 1.29 and 0.086 ng/ml, which is equivalent to essentially complete depyrogenation. The depyrogenated albumin solution was then subjected to ultrafiltration with a Millipore ® Cassette having a 10,000 molecular weight cutoff and using six volumes (i.e., 6×450 ml) of the diafiltration fluid (normal saline—0.9% NaCl). The retentate, which contained the albumin, and the permeate, which contained the Triton X-100 in saline, were both found to be essentially free of endotoxin (showing, respectively, 0.103 and 0.196 ng/ml endotoxin, which are not significantly different from the 1.29 and 0.086 ng/ml levels when compared with the about 100 ng/ml starting level of endotoxin.)

EXAMPLE 2

Depyrogenation of water followed by $CHCl_3$ extraction (a) A sample of water was spiked with 100 $\mu$g/ml of endotoxin from E. Coli. The sample was then treated with 0.1% Triton X-100 and incubated two hours at room temperature. The treated sample was extracted with an equal volume of chloroform and the aqueous phase was tested for endotoxin by the Limulus lysate amebocyte assay (LAL test). The LAL test was made on the aqueous phase at increasing dilutions until an endpoint was reached at which the test was negative in replicate tests (reached at 0.01 ng/ml titer level). In a qualitative test, the Triton X-100 was shown to have been removed by the chloroform extraction as evidenced by the absence of foaming upon shaking of the aqueous phase. The presence of said amphiphile is otherwise demonstrated by the appearance of foaming during such shaking.

(b) Substantially similar depyrogenation and removal of Triton X-100 is obtained when water-soluble pharmaceuticals are included in the aqueous solution being treated and when any of the following organic solvents are substituted for chloroform in part (a), above: methylene chloride, xylene and toluene.

EXAMPLE 3

The test procedure of Example 2 (a) was repeated except that the concentration of the Triton X-100 was 1% instead of 0.1%. In the LAL test on the aqueous phase after the chloroform extraction, the endpoint for negative testing for endotoxin in replicate tests was reached at the 0.05 ng/ml titer level.

EXAMPLE 4

Depyrogenation of antibiotic followed by $CHCl_3$ extraction (a) An antibiotic sample (dehydrostreptomycin sulfate, bulk) was reconstituted in aqueous solution to 100 mg/ml. The antibiotic solution was then treated with 1% Triton X-100 and incubated at room temperature for 1½ hours. The treated sample was extracted three times with equal volumes of chloroform (100 ml $CHCl_3$/100 ml sample each time) and the aqueous phase was then tested for antibiotic potency and endotoxin content. The antibiotic potency was 646 mg/g after treatment versus 638 mg/g for the untreated sample (no significant difference). The endotoxin content was reduced to between one and 1.13 ng/ml in the treated sample versus lying between 31 and 35 ng/ml in the untreated starting material in replicate tests.

(b) Similar results are obtained when butanol is substituted for chloroform in part (a) above.

EXAMPLE 5

Depyrogenation of DEAE-dextran beads followed by washing with isopropanol

Cross-linked dextran beads coated with diethylaminoethyl groups (DEAE) such as described in U.S. Pat. Nos. 4,189,534 and 4,293,654, and available from Flow Laboratories as "Superbeads", were placed in a phosphate buffered saline (PBS) suspension (100 ml beads). Triton X-100 was then added to a concentration of 2% and the suspension was mixed in a spinner flask for two hours. The beads were washed three times with equal volumes of the PBS. Considerable foaming was still observed after the third wash (indicating the presence of the Triton X-100). The beads were then washed with an equal volume of isopropanol and the foaming was then absent on shaking, thus indicating the removal of the Triton X-100. In LAL tests for endotoxin, the untreated beads were still positive when diluted 1:80 whereas the treated beads were negative even at a 1:1 dilution.

EXAMPLE 6

Depyrogenation of agarose

An aqueous suspension of 0.8% agarose was treated with 2% Triton X-100 and incubated two hours at room temperature. Treated and untreated samples of the agarose were then washed with saline and tested for endotoxin in the LAL test. The treated sample was negative while the untreated sample was positive both at 1:1 and 1:10 dilutions.

EXAMPLE 7

Depyrogenation of filtration membranes

Cellulosic filtration membranes (Nucleopore® F-100) were soaked in an aqueous solution containing 2% Triton X-100 (5 membranes in 30 ml solution). After an incubation period of two hours, the solution was decanted and 30 ml of pyrogen-free water was added. Incubation was continued for an additional 30 minutes. For control purposes, five other membranes were similarly treated in pyrogen-free water without the Triton X-100. The samples were tested for endotoxin in the LAL test and the Triton X-100 treated sample was found to be negative while the control sample was positive.

EXAMPLE 8

Depyrogenation of nylon fibers

Nylon threads (7 denier nylon 6.6 thread) and a roll of nylon tape (woven nylon 6.6 fabric) were soaked together in 2000 ml of an aqueous solution of 0.5% Triton X-100. The nylon was known by previous testing to contain from 500 to 750 pg endotoxin per ml of water extract when 2.5 g of thread were extracted with 40 ml of pyrogen-free water. The Triton X-100 treated nylon fiber sample was compared with a negative control of pyrogen-free water and a positive control containing 50 pg bacterial endotoxin per ml of solution. After incubation for two hours at room temperature, the negative control and the Triton X-100 treated sample were found to be negative while the positive control was still positive in the LAL test for pyrogens.

EXAMPLE 9

Depyrogenation of heparin followed by $CHCl_3$ extraction

A commercially supplied blood sample collection tube containing heparin anticoagulant for use at a blood donor center was found to be positive in the LAL test. The heparin was treated by the addition to the tube of an aqueous solution of 1% Triton X-100. The tube was allowed to stand one hour at room temperature, extracted with an equal volume of chloroform and allowed to stand an additional hour. The aqueous layer was observed to be slightly opalescent and when tested for pyrogens by the LAL test was found to be negative.

EXAMPLE 10

Thermal precipitation of Trixon X-100

An aqueous solution of 1% Triton X-100 after use for depyrogenation of a non-precipitable biomedical product or material is heated to its cloud point (about 65°-69° C.) after which a white precipitate is formed which can then be removed from the solution by phase separation.

EXAMPLE 11

Depyrogenation of vaccine

An experimental non-proteinaceous polysaccharide vaccine containing large amounts of endotoxin was depyrogenated by treatment with an aqueous solution of 3% Triton X-100 and incubation at room temperature for three hours. The vaccine was precipitated with polyethylene glycol 6000, resuspended in pyrogen-free water and tested for pyrogens by the LAL test. A fivefold reduction in pyrogens was confirmed.

EXAMPLE 12

Depyrogenation of cotton fibers

Cotton fibers which were loaded with endotoxin-producing gram negative bacteria were soaked in an aqueous solution of 5% Triton X-100 at 60° C. temperature for about 14 hours. The treated cotton fibers were then squeezed to wring out the aqueous solution and then allowed to dry. A 100-fold reduction in endotoxin in the treated cotton fibers was obtained by the above treatment.

Various other examples will be apparent to the person skilled in the art after reading this disclosure without departing from the spirit and scope of the invention and it is intended that all such examples be included in the scope of the appended claims.

What is claimed is:

1. The method of depyrogenating a biomedical product or material comprising treating said product or material by prolonged contact with a solution or suspension of about 0.1% to about 10% by weight of a nonionic amphiphile selected from the group consisting of substances having the general formula $RC_6H_4(OC_2H_4)_nOH$ wherein R is octyl or nonyl and n is at least 3, followed by separating said amphiphile from the resulting depyrogenated product or material by liquid phase separation.

2. The method of claim 1 in which the amphiphile is octyl phenoxy polyethoxy ethanol.

3. The method of claim 1 in which the liquid phase separation comprises solvent washing with isopropanol.

4. The method of claim 1 in which the liquid phase separation comprises solvent phase extraction with an organic solvent selected from the group consisting of butanol, chloroform, toluene, xylene and methylene chloride.

5. The method of claim 1 in which the liquid phase separation comprises ultrafiltration, diafiltration or dialysis.

6. The method of claim 5 in which the amphiphile is octyl phenoxy polyethyoxy ethanol.

7. The method of claim 1 in which the biomedical product or material is a filtration membrane.

8. The method of claim 1 in which the biomedical product or material is DEAE-coated cross-linked dextran beads.

9. The method of claim 4 in which the organic solvent is butanol.

* * * * *